US012146163B2

United States Patent
Kong et al.

(10) Patent No.: US 12,146,163 B2
(45) Date of Patent: Nov. 19, 2024

(54) VASCULARIZED CARDIAC ORGANOID WITH A CHAMBER STRUCTURE AND ITS PREPARATION METHOD

(71) Applicant: NANKAI UNIVERSITY, Tianjin (CN)

(72) Inventors: Deling Kong, Tianjin (CN);
Zhuangzhuang Yang, Tianjin (CN);
Songdi Wang, Tianjin (CN)

(73) Assignee: NANKAI UNIVERSITY, Tianjin (CN)

(*) Notice: Subject to any disclaimer, the term of this patent is extended or adjusted under 35 U.S.C. 154(b) by 0 days.

(21) Appl. No.: 18/381,652

(22) Filed: Oct. 19, 2023

(65) Prior Publication Data

US 2024/0132847 A1  Apr. 25, 2024
US 2024/0228967 A9  Jul. 11, 2024

(30) Foreign Application Priority Data

Oct. 19, 2022  (CN) .......................... 202211277761.2

(51) Int. Cl.
*C12N 5/077*  (2010.01)
(52) U.S. Cl.
CPC ........ *C12N 5/0657* (2013.01); *C12N 2500/32* (2013.01); *C12N 2501/115* (2013.01); *C12N 2501/165* (2013.01); *C12N 2501/998* (2013.01); *C12N 2513/00* (2013.01)
(58) Field of Classification Search
CPC .............. C12N 5/0657; C12N 2500/32; C12N 2501/115; C12N 2501/165; C12N 2501/998; C12N 2513/00
See application file for complete search history.

(56) References Cited

FOREIGN PATENT DOCUMENTS

| CN | 105025939 A | 11/2015 |
|---|---|---|
| CN | 112462380 A | 3/2021 |
| CN | 113699098 A | 11/2021 |
| CN | 114438021 A | 5/2022 |
| CN | 114891731 A | 8/2022 |
| WO | 2021123682 A1 | 6/2021 |
| WO | 2021257812 A1 | 12/2021 |

OTHER PUBLICATIONS

Kahn-Krell et al.(A three-dimensional culture system for generating cardiac spheroids composed of cardiomyocytes, endothelial cells, smooth-muscle cells, and cardiac fibroblasts derived from human induced-pluripotent stem cells. Front. Bioeng. Biotechnol. 10 :908848, Published Jul. 22, 2022; (Year: 2022).*
Song et al.(Assembly of Human Stem Cell-Derived Cortical Spheroids and Vascular Spheroids to Model 3-D Brain-like Tissues. Scientific Reports 9:5977, Apr. 2019) (Year: 2019).*
Burridge et al.(Chemically Defined and Small Molecule-Based Generation of Human Cardiomyocytes. Nat Methods. Aug. 2014 ; 11(8): 855-860) (Year: 2014).*
Sahni et al.(Stimulation of endothelial cell proliferation by FGF-2 in the presence of fibrinogen requires avb3. Blood, vol. 104, Dec. 2004) (Year: 2004).*
Nor et al.(Vascular Endothelial Growth Factor (VEGF)-Mediated Angiogenesis Is Associated with Enhanced Endothelial Cell Survival and Induction of Bcl-2 Expression. American Journal of Pathology, vol. 154, No. 2, Feb. 1999) (Year: 1999).*
ATCC Stem Cell Culture Guide (Year: 2022).*
Elisa Giacomelli, et al., Human-iPSC-Derived Cardiac Stromal Cells Enhance Maturation in 3D Cardiac Microtissues and Reveal Non-cardiomyocyte Contributions to Heart Disease, Cell Stem Cell, 2020, pp. 1-18, e1-e11, vol. 26.
Ana C. Silva, et al., Co-emergence of cardiac and gut tissues promotes cardiomyocyte maturation within human iPSC-derived organoids, Cell Stem Cell, 2021, pp. 2137-2152, e1-e6, 1-11,13, vol. 28.
Pablo Hofbauer, et al., Cardioids reveal self-organizing principles of human cardiogenesis, Cell, 2021, pp. 3299-3317, e1-e9, vol. 184.
Anna B. Meier, et al., Epicardioid single-cell genomics uncovers principles of human epicardium biology in heart development and disease, Nature Biotechnology, 2023.
Jiyoung Lee, et al., In vitro generation of functional murine heart organoids via FGF4 and extracellular matrix, Nature Communications, 2020, pp. 1-18, vol. 11, No. 4283.
Fan Si-Wen, et al., Establishment of 3D organoids model of cardiac hypertrophy and its application in the mechanistic analysis of cardiovascular traditional Chinese medicine, Acta Pharmaceutica Sinica, 2022, pp. 3067-3076, vol. 57, No. 10.
Leen Willems, et al., Differentiation of Human Cardiac Atrial Appendage Stem Cells into Adult Cardiomyocytes: A Role for the Wnt Pathway?, International Journal of Molecular Sciences, 2020, pp. 1-18, vol. 21, Article 3931.

* cited by examiner

*Primary Examiner* — Valarie E Bertoglio
*Assistant Examiner* — Matasha Dhar
(74) *Attorney, Agent, or Firm* — Bayramoglu Law Offices LLC (57) ABSTRACT

A vascularized cardiac organoid with a chamber structure and its preparation method is presented. The cardiac organoids have a unique chamber structure, which includes a myocardium wall. Within the cardiac organoids, a vascular network is developed, enclosed within the myocardium wall. This vascular network is composed of endothelial cells surrounded by smooth muscle cells, forming a network of branched tubular structures. The presence of vasculature significantly promotes the arrangement of the myocardium, enhances the organization of the cardiac cytoskeleton, and promotes the consistency and beating frequency of cardiac cells. The vasculature facilitates the growth and size increase of the cardiac organoids.

5 Claims, 10 Drawing Sheets

FIG. 1a

Vascular spheroid

VASCULARIZED CARDIAC ORGANOID WITH A CHAMBER STRUCTURE AND ITS PREPARATION METHOD

CROSS-REFERENCE TO RELATED APPLICATIONS

This application is based upon and claims priority to Chinese Patent Application No. 202211277761.2, filed on Oct. 19, 2022, the entire contents of which are incorporated herein by reference.

TECHNICAL FIELD

The present invention belongs to the field of organoid preparation technology, particularly to a vascularized cardiac organoid with a chamber structure and a preparation method thereof.

BACKGROUND OF THE INVENTION

Cardiovascular diseases are the leading cause of mortality worldwide and poses a significant risk of morbidity and threat to human health. Developing an effective model to investigate cardiovascular disease pathogenesis is instrumental in developing effective interventions to potentially save millions of lives per year. While 2D cultured cardiomyocytes or vascular cells are frequently employed as models, they fall short in replicating the intricate structure of organs. Mouse models, extensively utilized to study cardiovascular diseases, have genomes that differ from humans, making it challenging to study specific functions of disease-causing genes with precise relevance to human cardiovascular disease pathogenesis and progression. Consequently, it is of utmost importance to construct appropriate cardiac models to comprehensively understand the physiological and pathological processes in a human context.

In recent years, there have been significant advancements in the construction of organoids using human induced pluripotent stem cells (iPSCs). These organoids successfully replicate the key cellular components of respective organs and accurately recapitulate their 3D tissue structures. Organoids have emerged as invaluable tools for studying physiological and pathological processes. Among all organs, the heart presents a prominent challenge in the creation of in vitro models, due to its intricate structure and diverse cell types. In 2019, Jiyoung Lee et al. reported the groundbreaking achievement of in vitro construction of mouse cardiac organoids. As of 2023, only a handful of reports of human cardiac organoids have been successfully generated, all of which have been published in prestigious journals such as *Cell, Cell Stem Cell, Nature Biotechnology, and Nature Communications*. Although the number of reported cases is limited, these studies have demonstrated the tremendous potential of cardiac organoids in investigating heart development, diseases modeling, and drug screening.

The heart, characterized by its multi-chamber structure and intricate cellular components, presents a unique challenge to its recreation using biomedical research methodology. Previous studies have employed various techniques such as molds, scaffold materials, and hydrogels to construct cardiac tissues. These approaches have proven useful in exploring myocardial contractility, electrophysiology, drug screening, and arrhythmogenic disorders. However, most of these methods fall short in their accurate mimicking of the chamber structure and complex morphology of the heart. Therefore, the development of cardiac organoids that can replicate the chamber structure holds significant promise for advancing heart research and enables a more comprehensive understanding of heart biology.

Achieving vascularization presents a critical challenge in the construction of organoids. Currently, organoids lack well-developed vascular networks, which becomes increasingly problematic as the organoids grow in size. Without sufficient vascularization, the central and innermost cells of larger organoids undergo apoptosis due to inadequate nutrient and oxygen supply. Previous attempts have employed endothelial cells (ECs), vascular smooth muscle cells (VSMCs), and mesenchymal stem cells (MSCs) to construct microvascular fragments. Additionally, adipose tissue-derived microvascular fragments have been utilized. The use of these microvascular fragments has encountered obstacles such as tissue heterogeneity, low efficiencies, irregular endothelial cell colonies, and incomplete formation of vascular structures. Moreover, there is limited research on the impact of vascularization applied to the morphogenesis and functionality of cardiac organoids.

However, studies have shown that vasculature is essential for heart function, morphogenesis, and metabolic maturation. Therefore, the innovative development of a vascularized cardiac organoid with a chamber structure holds immense significance in terms of its application in exploring heart development, drug screening, pathogenesis, and heart regeneration.

BRIEF SUMMARY OF THE INVENTION

The goal of this invention is to construct a vascularized cardiac organoid with a chamber structure. This organoid is characterized by an internal chamber structure, a myocardium wall that integrates functional vascular networks and spontaneously contracts at a frequency comparable to that of the human heart.

A preparation method of a vascularized cardiac organoid with a chamber structure comprises the following steps:
  Step 1: select stem cells A and stem cells B for in vitro culture and maintenance; wherein, stem cells A have potential of vascular lineage cell differentiation, and stem cells B have potential of cardiomyocyte differentiation;
  Step 2: differentiate stem cells A into vascular spheroids and stem cells B into cardiac spheroids;
  Step 3: fuse one or more vascular spheroids with one or more cardiac spheroids and culture them to form vascularized cardiac organoids.

Further, the stem cells A and stem cells B are sourced from human or animal-induced pluripotent stem cells (iPSCs), embryonic stem cells, or adult stem cells;

Further, the pluripotent stem cells, in general, are human or animal-induced pluripotent stem cells, embryonic stem cells, or other cells with totipotency.

Preferably, the density of the pluripotent stem cells, which are maintained in stem cell medium, is 80% before passage.

Preferably, the stem cell medium used is Essential 8 or mTeSR1.

Preferably, hiPSCs were disassociated into a single-cell suspension using 0.5 mM EDTA or Accutase at room temperature or 37° C. for 6-8 minutes.

Further, in step 1, the preparation process of vascular spheroids involves culturing stem cells A into spheroids and then differentiating them into vascular spheroids; alternatively, differentiating stem cells A into vascular cells under 2D conditions and then being assembled into spheroids.

Further, in step 2, the preparation process of cardiac spheroids involves culturing stem cells B into spheroids and then differentiating them into cardiac spheroids; alternatively, differentiating stem cells B into cardiomyocytes under 2D conditions and then being assembled into spheroids.

Preferably, when the spheroids are derived from the pluripotent stem cells, the stem cells are cultured into embryoid bodies (EBs) and then divided into two parts, each part is then differentiated into vascular spheroids and cardiac spheroids, respectively.

Further, in the fusion process described in step 3, vascular spheroids and cardiac spheroids can be fused under normal culture conditions, suspension culture conditions, or with the assistance of embedding materials such as hydrogels.

Preferably, the fusion process is conducted under suspension culture conditions.

Further, in step 3, the number of cardiac spheroids should be between 1 and 4.

Further, in step 3, the number of vascular spheroids should be between 1 and 10.

Preferably, in step 3, the number of cardiac spheroids is 1, the number of the vascular spheroids is 1.

Further, in step 3, the culture process should continue for a period of 3-5 days.

Preferably, the chemically defined medium for vascular spheroids induction is CDM3-V (consisting of Roswell Park Memorial Institute 1640 Medium (RPMI 1640), 1 mg/mL bovine serum albumin (BSA) and 150 μg/mL L-ascorbic acid (LAA)); for day 0 to day 2, the medium was supplemented with 6 μM CHIR99021, on day 2, the medium was changed to CDM-V supplemented with 50 ng/ml vascular endothelial growth factor (VEGF) and 25 ng/mL fibroblast growth factor 2 (FGF2), then refreshed every other day until day 10.

Preferably, the chemically defined medium for cardiac spheroids induction is CDM3-C (consisting of RPMI 1640, 500 μg/mL BSA and 200 μg/mL LAA). For day 0 to day 2, the medium was supplemented with 6 μM CHIR99021; from day 2 to day 4, the medium was changed to CDM3-C supplemented with 6 μM IWR; on day 4, the medium was changed to CDM3-C then refreshed every other day until day 8.

Preferably, an induction system under chemically defined conditions is constructed to cultivate EBs into vascular and cardiac spheroids.

Preferably, different sizes of vascular and cardiac spheroids can be achieved by differentiating the initiation time of differentiation, the differentiation time of vascular cells is earlier than that of cardiomyocytes; this approach allows for the recapitulation of organ development principles.

Preferably, the simultaneous termination of differentiation in both spheroids facilitates their subsequent fusion and the formation of organoids.

Preferably, the culture medium for vascularized cardiac organoids consists of CDM3-C supplemented with 50 ng/mL VEGF, 25 ng/mL FGF2, and 20% fetal bovine serum (FBS); this medium promotes spheroid bonding and enhances cell survival.

Preferably, the content of the FBS in the medium with definite composition for vascularized cardiac organoids is 2.5% in order to reduce the influence of uncertain components in serum on the study in subsequent application.

This present invention discloses a vascularized cardiac organoid with a chamber structure, which is prepared by using the aforementioned method.

The invention offers the following benefits:
1. The prepared vascularized cardiac organoids demonstrate evident chamber structures and form myocardial walls;
2. A distinct vascular network is formed within the prepared myocardial walls of the vascularized cardiac organoids. The benefits of this vasculature encompasses lumen formation and the facilitation of interactions between endothelial cells and smooth muscle cells;
3. The presence of vasculature promotes the alignment of cardiomyocytes, enhances the organization of cardiac cell cytoskeletons, and increases the consistency and frequency of cardiomyocyte contractions;
4. Vasculature contributes to the enlargement of cardiac organoid size.

BRIEF DESCRIPTION OF THE FIGURES

FIG. 5 shows immunofluorescence staining for cTNT and statistics analysis of cardiac spheroids and organoids of example 1. FIG. 5; wherein.

FIG. 8 shows cardiomyocytes differentiation of hiPSCs under 2D culture conditions and their identification.

DETAILED DESCRIPTION OF THE INVENTION

The following examples are provided to further describe the concrete implementation of the invention. These examples are used solely to clarify the technical aspects of the invention and do not limit the scope of protection.

EXAMPLE 1

Figure 1A:
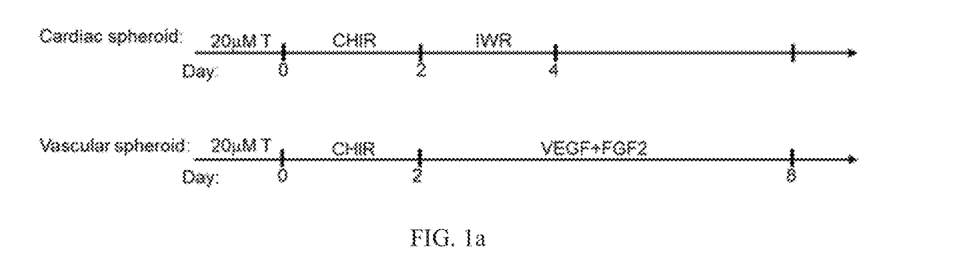
FIG. 1a is an induction diagram of vascular and cardiac spheroids, respectively, wherein the upper part shows the iPSCs-derived vascular spheroids of example 1, the lower part shows the iPSCs-derived cardiac spheroids of example 1.

A preparation method of a vascularized cardiac organoid with a chamber structure, both vascular and cardiac spheroids are induced following the formation of embryoid bodies (EBs), and includes the following steps:

(1) The human induced pluripotent stem cells (hiPSCs) are dissociated into a single-cell suspension and then transferred into ultra-low attachment plates at a ratio of 1:3, and cultured for one day by using a stem cell culture medium to allow the formation of EBs, on day 2, the EBs are divided into two parts;

(2) To differentiate one of the EBs into cardiac spheroids, from day 5, a cardiac spheroid inducing system with chemically defined conditions is adopted for 8 days. The induction medium for cardiac spheroids is CDM3-C, wherein, RPMI 1640 as a basic culture medium, and 500 μg/mL BSA and 200 μg/mL LAA are added. From day 0 to day 2, the medium is supplemented with 6 μM CHIR99021. From day 2 to day 4, the medium is changed to CDM3-C supplemented with 6 μM IWR. On day 4, the medium is changed back to CDM3-C and refreshed every other day until day 8. (FIG. 1a shows the schematic of cardiac spheroids differentiation).

Figure 1B:
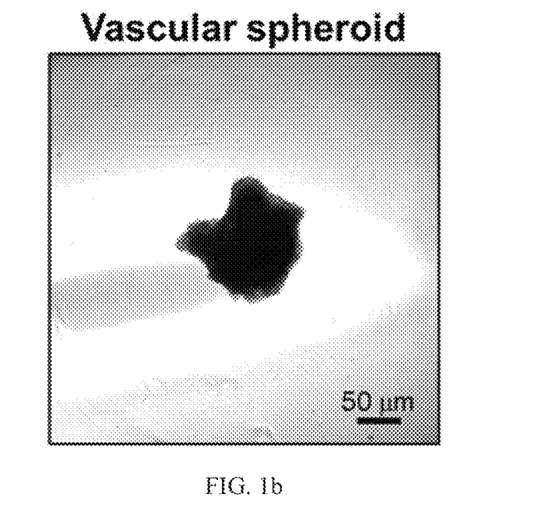
FIG. 1b shows the brightfield photographs of vascular spheroids.
Figure 1C:
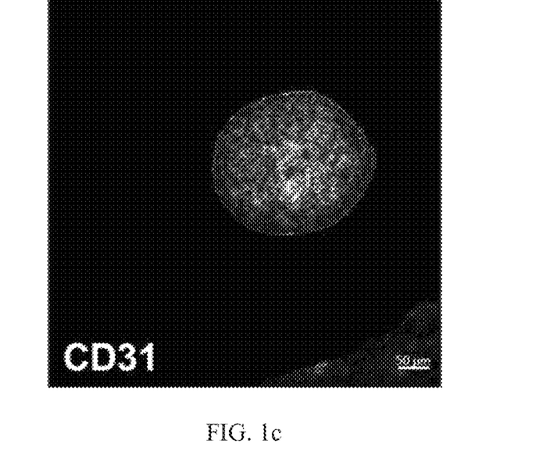
FIG. 1c shows immunofluorescence staining for CD31 of vascular spheroids.
Figure 1D:
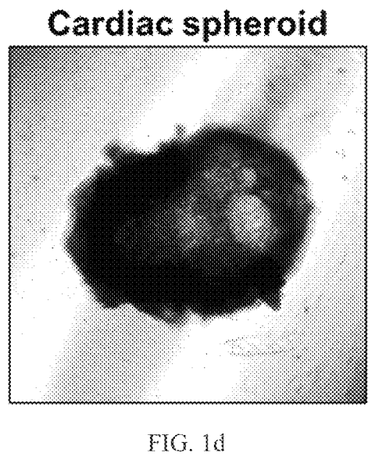
FIG. 1d shows the brightfield photographs of cardiac spheroids of example 1.
Figure 1E:
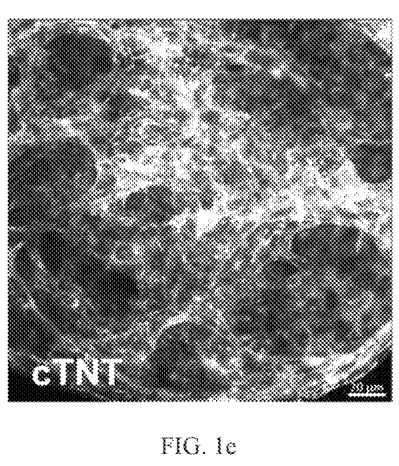
FIG. 1e shows immunofluorescence staining for cTNT of cardiac spheroids of example 1.

(3) Immunofluorescence staining shows that cardiomyocytes express the cardiac specific marker troponin-T (cTNT) (as shown in FIG. 1d, 1e);

(4) To differentiate another part of the EBs into vascular spheroids, from day 3, a vascular spheroid inducing system with chemically defined conditions is adopted for 10 days. The induction medium for vascular spheroids is CDM3-V, wherein RPMI 1640 as a basic culture medium, and 1 mg/mL BSA and 150 μg/mL LAA are added. From day 0 to day 2, the medium is supplemented with 6 μM CHIR99021. On day 2, medium is changed to CDM3-V supplemented with 50 ng/mL VEGF and 25 ng/mL FGF2, then refreshed medium every other day until day 10.

(5) Immunofluorescence staining shows that vascular spheroids express endothelial cell specific marker CD31 (FIG. 1b, 1c).

(6) On day 10, one of cardiac spheroids and one of the vascular spheroids are transferred into one well of ultra-low attachment 96-well plate.

(7) During the first 3 days after inoculation, the vascularized cardiac organoids are cultured in CDM3-O medium supplemented with 20% FBS to promote spheroid bonding and enhance cell survival, wherein the culture medium for vascular spheroids is CDM3-O, wherein RPMI 1640 as a basic culture medium, and 500 μg/mL BSA, 200 μg/mL LAA, 50 ng/mL VEGF and 25 ng/ml FGF2 are added.

(8) Starting from day 4, the FBS content in the medium for the vascularized cardiac organoids is decreased to 2.5%.

Figure 2:
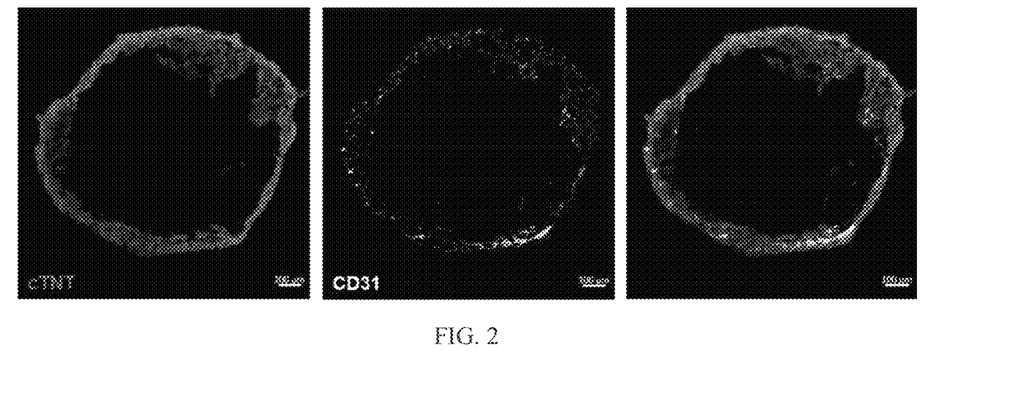
FIG. 2 shows immunofluorescence staining of cardiac organoids of example 1, wherein the first drawing is immunostaining of cardiomyocytes, the second drawing is immunostaining of vascular cells, the third drawing is merged immunostaining of cardiomyocytes and vascular cells.
Figure 3:
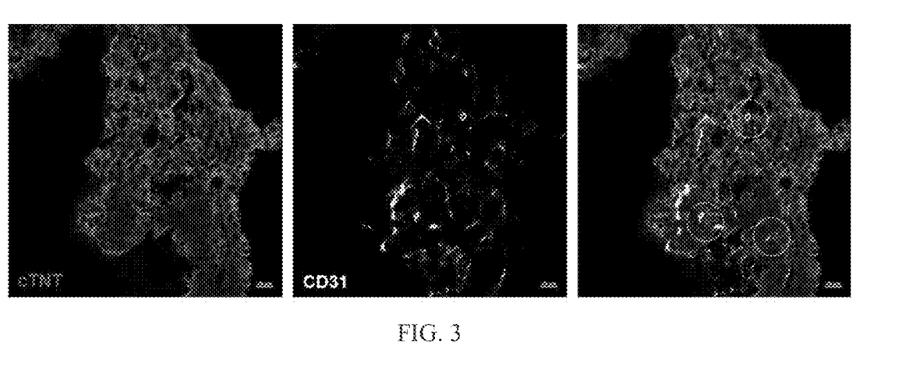
FIG. 3 shows local amplified immunofluorescence staining of cardiac organoids of example 1, the first drawing is a staining of cardiomyocytes, the second drawing is immunostaining of vascular cells, the third drawing is merged immunostaining of cardiomyocytes and vascular cells.

(9) On day 5 after implantation, vascularized cardiac organoids with a typical chamber structure are obtained. Immunofluorescence staining of frozen sections reveal a complete chamber structure in the center of these organoids, with the outer layer consisting of myocardium (marked by cTNT positivity) interspersed with a network of blood vessels (marked by CD31 positivity) (FIGS. 2, 3); a typical chamber structure can be observed through cross-section immunofluorescence staining (FIG. 3 white dotted line).

Figure 4:
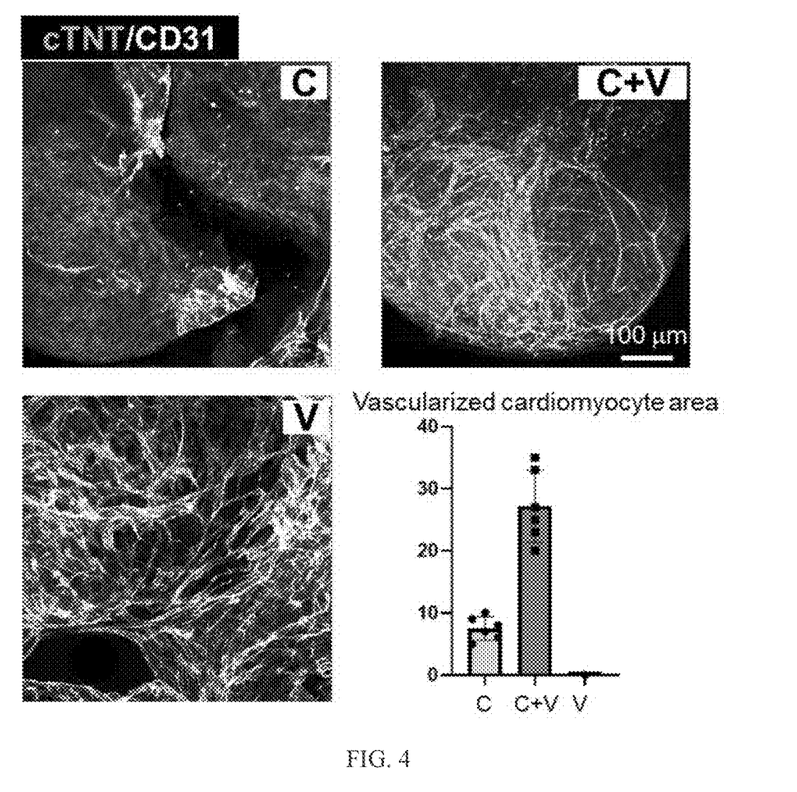
FIG. 4 shows immunofluorescence for cardiac spheroid, vascular spheroid and vascularized cardiac organoid and the statistics of vascularized cardiomyocytes area of example 1; wherein the group "C" is cardiac spheroid, group "V" is vascular spheroid and group "C+V" is fusion of cardiac and vascular spheroids.

(10) To quantify the vascularization of the organoids, cardiac spheroids, vascular spheroids, and vascularized cardiac organoids are compared. By staining the microvascular network (marked by CD31 positivity), the percentage of vascularized cardiomyocytes in the vascularized cardiac organoids are observed, showing approximately 28%, whereas cardiac spheroids exhibit only 8%. This finding demonstrates that this vascularization method significantly enhances the degree of vascularization in cardiac spheroids (as shown in FIG. 4).

Figure 5A:
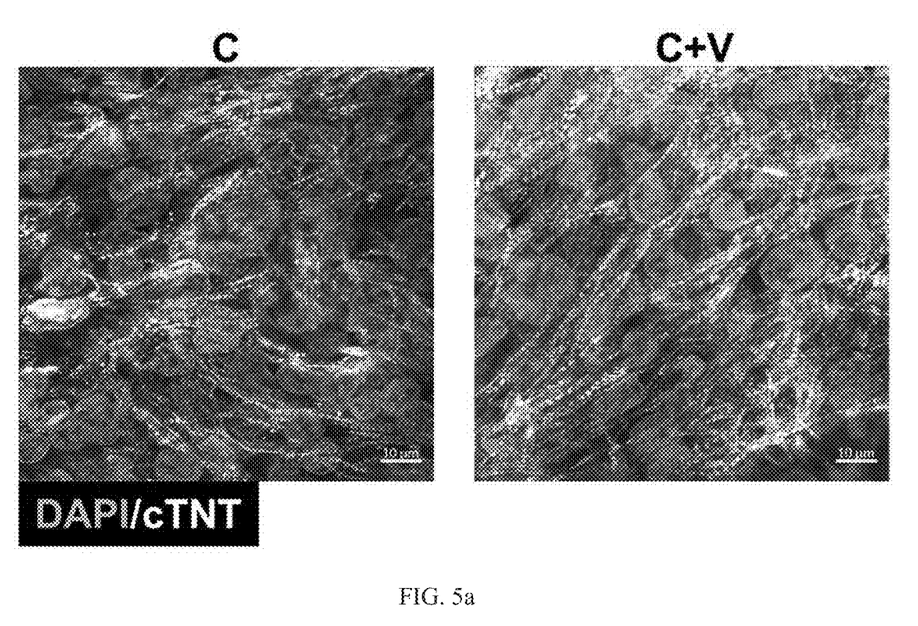
FIG. 5a shows cTNT immunofluorescence staining of cardiomyocytes.
Figure 5B:
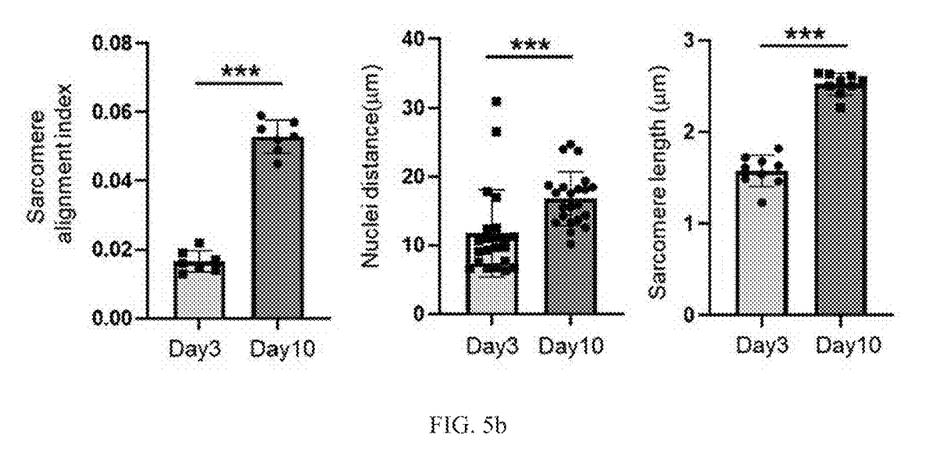
FIG. 5b is statistics of sarcomere alignment index, nuclear distance and sarcomere length respectively, the first drawing is statistics of sarcomere alignment index, the second drawing is nuclear distance and the third drawing is sarcomere length.

(11) The impact of vasculature on the cellular structure and function of cardiomyocytes are analyzed. Immunofluorescence staining demonstrates that vasculature promotes alignment of cardiomyocytes (as shown in FIGS. 5a, 5b).

Figure 6:
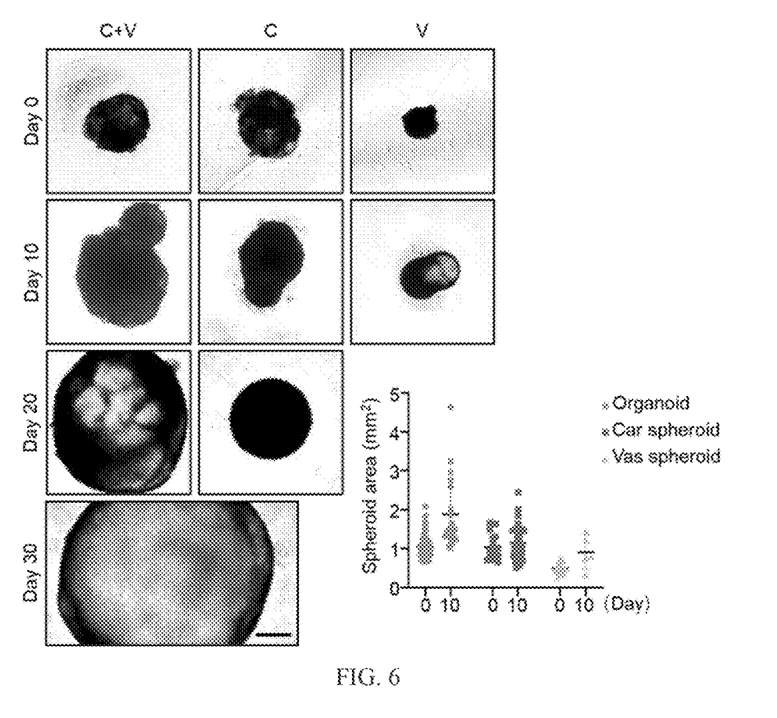
FIG. 6 shows the brightfield photographs and statistical diagrams of the volume growth over time of the vascularized cardiac organoids in example 1. Wherein the group "C" is cardiac spheroid, group "V" is vascular spheroid and group "C+V" is fusion of cardiac and vascular spheroids.

(12) Upon continuous culture of the obtained vascularized cardiac organoids, it is observed that vasculature facilitates the sustained growth of cardiac organoids (as shown in FIG. 6).

Figure 7:
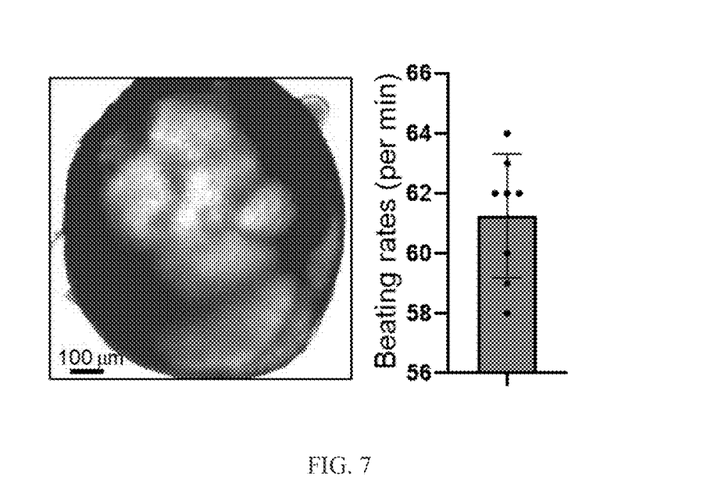
FIG. 7 is a statistical diagram showing the brightfield photograph of cardiac organoids on day 30 and the statistical analysis of beating rates in example 2.

(13) The beating rate/minute of the vascularized cardiac organoids are obtained on day 30 and the rates resemble those of a human heartbeat (as shown in FIG. 7), indicating that the organoids mature further during continuous culture. This finding further corroborates the aforementioned results.

EXAMPLE 2

A preparation method of a vascularized cardiac organoid with a chamber structure, wherein vascular spheroids are induced by EBs and cardiac spheroids are obtained by aggregation of cardiomyocytes induced under 2D culture conditions, includes the following steps:

(1) Human embryonic stem cells (H1 cell line) are dissociated into a single-cell suspension and then transferred into ultra-low attachment plates at a ratio of 1:3, and cultured for one day by using a stem cell culture medium PE8 to allow the formation of EBs, and them induction of vascular spheroids is performed as shown in example 1.

(2) To differentiate the EBs into vascular spheroids, from day 5, a vascular spheroid inducing system with chemically defined conditions is adopted for 8 days. The induction medium for vascular spheroids is CDM3-V, wherein RPMI 1640 as a basic culture medium, 1 mg/mL BSA and 150 μg/mL LAA are added. From day 0 to day 2, the medium is supplemented with 6 μM CHIR99021. On day 2, medium is changed to CDM3-V supplemented with 50 ng/mL VEGF and 25 ng/ml FGF2, then refreshed medium every other day until day 10.

(3) Immunofluorescence staining shows that vascular spheroids express endothelial cell specific marker CD31 (as shown in FIGS. 1b, 1c);

(4) To induce the H1 embryonic stem cells into cardiomyocytes, cell splitting is performed and the cells are subsequently transplanted into Matrigel-coated plates at a ratio of 1:6, using PE8 medium for a duration of 3 days. Cardiomyocytes began to differentiate once the cells reach approximately 80% confluence. The medium used for cardiomyocyte induction has a chemically defined composition known as CDM3-C, which comprises RPMI 1640 supplemented with 500 µg/mL BSA and 200 µg/mL LAA.

Figure 8A:
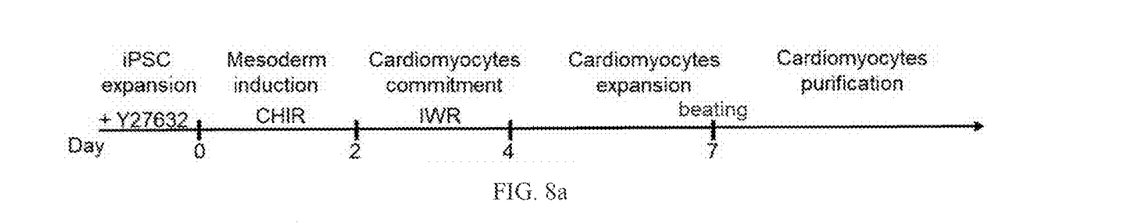
FIG. 8a is schematic diagram of iPSC-derived cardiomyocytes under 2D culture conditions.
Figure 8B:
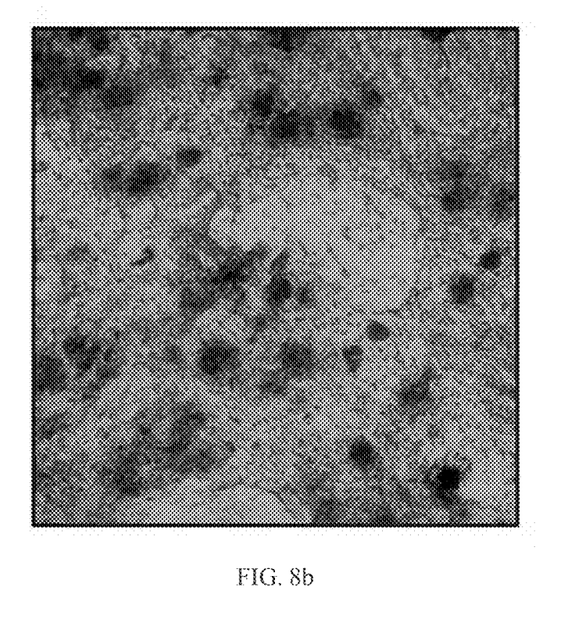
FIG. 8b is the brightfield photographs of cardiomyocytes induced under 2D culture conditions on day 7.
Figure 8C:
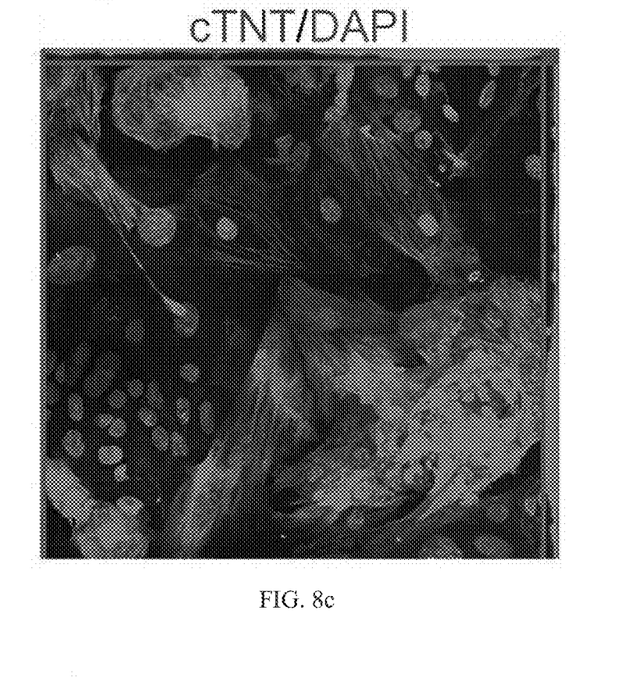
FIG. 8c is immunofluorescence staining of cTNT for cardiomyocytes induced under 2D culture conditions on day 7.
Figure 8D:
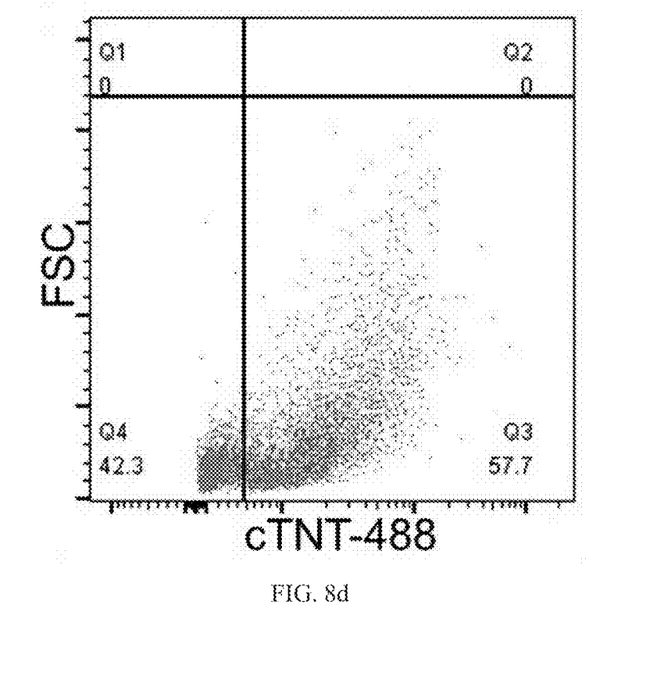
FIG. 8d is the flow cytometry analysis of cardiomyocytes induced under 2D culture conditions on day 7, labeled by cTNT.
Figures 10A, 10B:
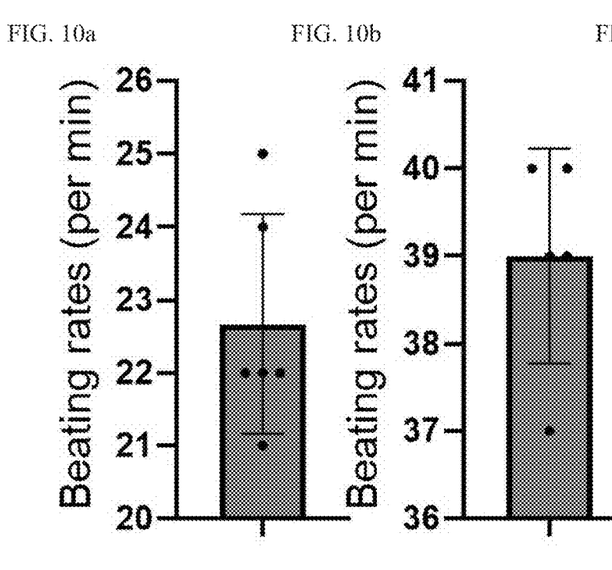
FIG. 10a is the statistical analysis of beating rates of organoids on day 19 in examples 2.
FIG. 10b is the statistical analysis of beating rates of organoids on day 19 in examples 3.

(5) From day 0 to day 2, the medium is supplemented with 6 µM of CHIR99021. Starting from day 2 until day 4, the medium is replaced with CDM-C supplemented with 6 µM IWR. On day 4, the medium is changed to CDM-C and subsequently refreshed every other day until day 7 when the cardiomyocytes begin to spontaneously contract (as shown in FIGS. 10a, 10b). Immunofluorescence staining reveals that the majority of differentiated cells express the cardiomyocyte specific marker cTNT (as shown in FIG. 8c), and the flow cytometry analysis shows a positive rate of cTNT expression at approximately 60% of the total number of cells (as shown in FIG. 8d).

(6) A purification procedure is utilized to obtain highly pure cardiomyocytes. The purification medium takes RPMI 1640 without glucose as a basic medium, and 500 µg/mL BSA, 200 µg/mL LAA, and 5 mM Lactate are added.

Figure 8E:
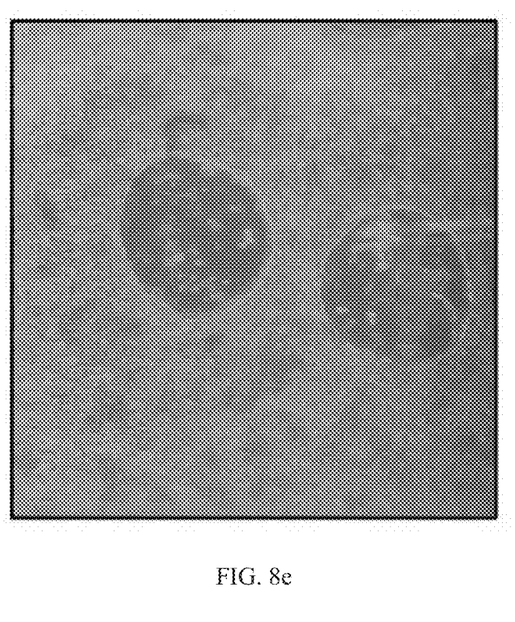
FIG. 8e is the brightfield photographs of cardiomyocytes induced under 2D culture conditions on day 10.
Figure 8F:
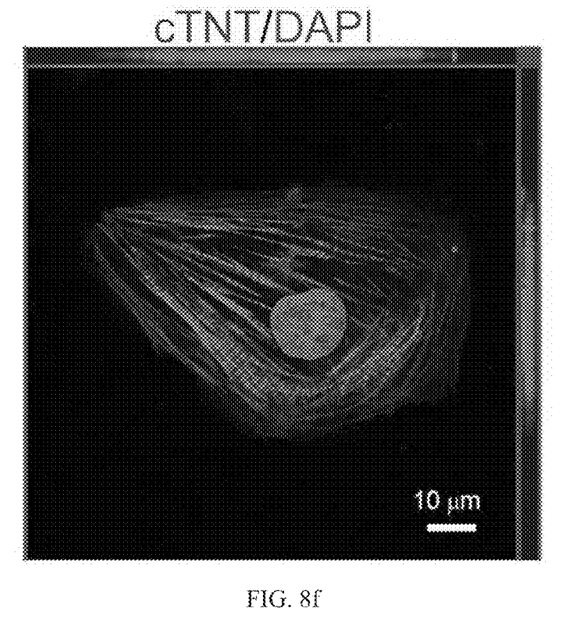
FIG. 8f is immunofluorescence staining for cTNT of cardiomyocytes induced under 2D culture conditions on day 10.
Figure 8G:
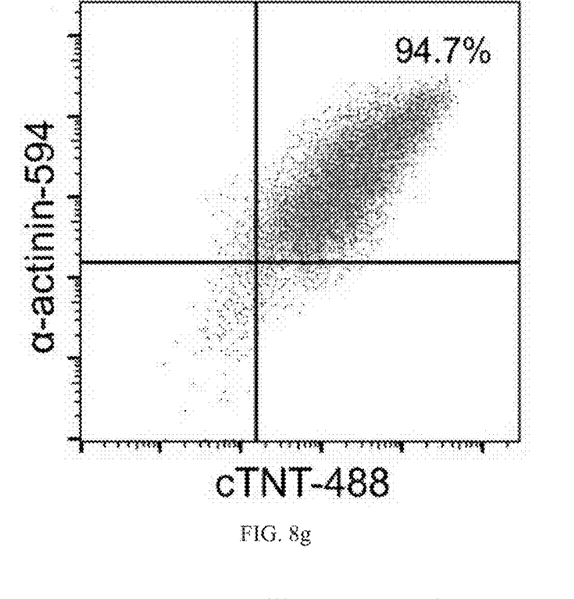
FIG. 8g is the flow cytometry analysis of cardiomyocytes induced under 2D culture conditions on day 10.

(7) After a 10-day purification process, highly pure cultures of beating cardiomyocytes are obtained (as shown in FIG. 8e). Immunofluorescence staining reveals that nearly all of the purified cells express the cardiomyocyte-specific marker cTNT (as shown in FIG. 8f). Additionally, flow cytometry analysis shows that over 94% of the cells are positive for cTNT (as shown in FIG. 8g).

(8) 0.25% of pancreatin is added into the purified cell, and then are put into a cell incubator for digestion for 10-15 mins, a CMD-C medium containing 10% FBS is adopted to dissociate the differentiated cardiomyocytes into a single cell suspension and then transplanted into low attachment 96-well plates at a density of 0.5×10^4 cardiomyocytes per well. They are then incubated overnight to form cardiac spheroids.

(9) On the second day, a fully differentiated vascular spheroid is transferred into the well containing a cardiac spheroid.

(10) For the first 3 days following incorporation, the vascularized cardiac organoids are cultured in CDM3-O medium supplemented with 20% FBS to promote spheroid bonding and facilitates cell survival; wherein the culture medium is CDM3-O, wherein RPMI 1640 as basic culture medium, and 500 µg/mL BSA, 200 µg/mL LAA, 50 ng/mL VEGF, 25 ng/ml FGF2 are added.

(11) From day 4 onwards, the FBS content in the medium of vascularized cardiac organoids is reduced to 2.5%.

Figure 9A:
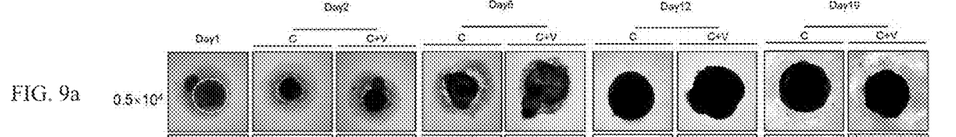
FIG. 9a is the brightfield photographs of organoids over time in examples 2.

(12) The beating rate/minute of the obtained vascularized cardiac organoids on day 19 reaches approximately 30 beats per minute (as shown in FIGS. 9a, 10a).

EXAMPLE 3

A preparation method of a vascularized cardiac organoid with a chamber structure, wherein vascular spheroids are induced by EBs and cardiac spheroids are obtained by the aggregation of cardiomyocytes induced under 2D culture conditions, includes the following steps:

(1) Human embryonic stem cells (H1 cell line) are dissociated into a single-cell suspension and then transferred into ultra-low attachment plates at a ratio of 1:3, and are cultured for one day by using PE8 medium to allow the formation of EBs; and them induction of vascular spheroids is performed as shown in example 1.

(2) To differentiate the EBs into vascular spheroids, from day 5, a vascular spheroid inducing system with chemically defined conditions is adopted for 8 days. The induction medium for vascular spheroids is CDM3-V, wherein RPMI 1640 as a basic culture medium, and 1 mg/mL BSA and 150 µg/mL LAA are added. From day 0 to day 2, the medium is supplemented with 6 µM CHIR99021. On day 2, medium is changed to CDMe-V supplemented with 50 ng/mL VEGF and 25 ng/ml FGF2, then refreshed medium every other day until day 10 (as shown in FIG. 1a).

(3) Immunofluorescence staining shows that vascular spheroids express endothelial cell specific marker CD31 (as shown in FIG. 1b, 1c);

(4) To induce the H1 embryonic stem cells into cardiomyocytes, cell splitting is performed and the cells are subsequently transplanted into Matrigel-coated plates at a ratio of 1:6, using PE8 medium for a duration of 3 days. Cardiomyocytes begin to differentiate once the cells reach approximately 80% confluence (as shown in FIG. 8). The medium used for cardiomyocyte induction is a chemically defined composition known as CDM3-C, which comprises RPMI 1640 supplemented with 500 µg/mL BSA and 200 µg/mL LAA.

(5) From day 0 to day 2, the medium is supplemented with 6 µM of CHIR99021. Starting from day 2 until day 4, the medium is replaced with CDM3-C supplemented with 6 µM IWR. On day 4, the medium is changed to CDM-C and subsequently refreshed every other day until day 7, when the cardiomyocytes begin to spontaneously contract. Immunofluorescence staining reveals that a majority of the differentiated cells express the cardiomyocyte specific marker cTNT (as shown in FIG. 8c), and the flow cytometry analysis shows a positive cTNT expression rate of approximately 57% of the total number of cells (as shown in FIG. 8d).

(6) A purification procedure is utilized to obtain highly pure cardiomyocytes. The purification medium takes RPMI 1640 without glucose as a basic medium, and 500 µg/mL BSA, 200 µg/mL LAA, and 5 mM Lactate are added.

(7) After a 10-day purification process, highly pure cultures of beating cardiomyocytes are obtained. Immunofluorescence staining reveals that nearly all of the purified cells express the cardiomyocyte-specific marker cTNT (as shown in FIG. 8f). Additionally, flow cytometry analysis shows that over 94% of the cells are positive for cTNT (as shown in FIG. 8g).

(8) 0.25% of pancreatin is added into the purified cell, and then are put into a cell incubator for digestion for 10-15 mins, a CMD-C medium containing 10% FBS is adopted to dissociate the differentiated cardiomyocytes into a single cell suspension and then transplanted into low attachment 96-well plates at a density of 1×10^4 cardiomyocytes per well. They are incubated overnight to form cardiac spheroids;

(9) On the second day, a fully differentiated vascular spheroid is transferred into the well containing a cardiac spheroid;

(10) For the first 3 days following incorporation, the vascularized cardiac organoids are cultured in CDM3-O medium supplemented with 20% FBS to promote spheroid bonding and facilitates cell survival; wherein the culture medium is CDM3-O, wherein RPMI 1640 as basic culture medium, and 500 μg/mL BSA, 200 μg/mL LAA, 50 ng/mL VEGF, 25 ng/mL FGF2 are added.

(11) From day 4 onwards, the FBS content in the medium of vascularized cardiac organoids is reduced to 2.5%.

Figure 9B:
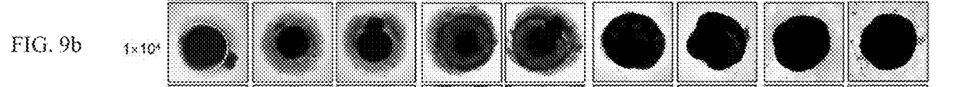
FIG. 9b is the brightfield photographs of organoids over time in examples 3.

(12) The beating rate/minute of the obtained vascularized cardiac organoids on day 19 reaches approximately 30 beats per minute (as shown in FIGS. 9b, 10b).

EXAMPLE 4

A preparation method of a vascularized cardiac organoid with a chamber structure, wherein vascular spheroids are induced by EBs and cardiac spheroids are obtained by the aggregation of cardiomyocytes induced under 2D culture conditions, includes the following steps:

(1) Human embryonic stem cells (H1 cell line) are dissociated into a single-cell suspension and then transferred into ultra-low attachment plates at a ratio of 1:3, and are cultured for one day by using PE8 medium to allow the formation of EBs; and them induction of vascular spheroids is performed as shown in example 1.

(2) To differentiate the EBs into vascular spheroids, from day 5 a vascular spheroid inducing system with chemically defined conditions is adopted for 8 days. The induction medium for vascular spheroids is CDM3-V, wherein RPMI 1640 as a basic culture medium, and 1 mg/mL BSA and 150 μg/mL LAA are added. From day 0 to day 2, the medium is supplemented with 6 μM CHIR99021. On day 2, medium is changed to CDMe-V supplemented with 50 ng/mL VEGF and 25 ng/ml FGF2, then refreshed medium every other day until day 10 (as shown in FIG. 1a).

(3) Immunofluorescence staining shows that vascular spheroids express endothelial cell specific marker CD31 (as shown in FIGS. 1b, 1c);

(4) To induce the H1 embryonic stem cells into cardiomyocytes, cell splitting is performed and the cells are subsequently transplanted into Matrigel-coated plates at a ratio of 1:6, using PE8 medium for a duration of 3 days. Cardiomyocytes begin to differentiate once the cells reach approximately 80% confluence (as shown in FIG. 8). The medium used for cardiomyocyte induction is a chemically defined composition known as CDM3-C, which comprises RPMI 1640 supplemented with 500 μg/mL BSA and 200 μg/mL LAA.

(5) From day 0 to day 2, the medium is supplemented with 6 μM of CHIR99021. Starting from day 2 until day 4, the medium is replaced with CDM-C supplemented with 6 μM IWR. On day 4, the medium is changed to CDM-C and subsequently refreshed every other day until day 7, when the cardiomyocytes began to spontaneously contract. Immunofluorescence staining reveals that the majority of the differentiated cells express the cardiomyocyte specific marker cTNT (as shown in FIG. 8c), and the flow cytometry analysis shows a positive cTNT expression rate of approximately 57% of the total number of cells (as shown in FIG. 8d).

(6) A purification procedure is utilized to obtain highly pure cardiomyocytes. The purification medium takes RPMI 1640 without glucose as a basic medium, and 500 μg/mL BSA, 200 μg/mL LAA, and 5 mM Lactate are added.

(7) After a 10-day purification process, highly pure cultures of beating cardiomyocytes are obtained. Immunofluorescence staining reveals that nearly all of the purified cells express the cardiomyocyte-specific marker cTNT (as shown in FIG. 8f). Additionally, flow cytometry analysis shows that over 94% of the cells were positive for cTNT (as shown in FIG. 8g).

(8) 0.25% of pancreatin is added into the purified cell, and then are put into a cell incubator for digestion for 10-15 mins, a CMD-C medium containing 10% FBS is adopted to dissociate the differentiated cardiomyocytes into a single cell suspension and then transplanted into low attachment 96-well plates at a density of $1 \times 10^{5}$ cardiomyocytes per well. They are incubated overnight to form cardiac spheroids;

(9) On the second day, a fully differentiated vascular spheroid is transferred into the well containing a cardiac spheroid;

(10) For the first 3 days following incorporation, the vascularized cardiac organoids are cultured in CDM3-O medium supplemented with 20% FBS to promote spheroid bonding and facilitates cell survival; wherein the culture medium is CDM3-O, wherein RPMI 1640 as basic culture medium, and 500 μg/mL BSA, 200 μg/mL LAA, 50 ng/mL VEGF, 25 ng/ml FGF2 are added.

(11) From day 4 onwards, the FBS content in the medium of vascularized cardiac organoids is reduced to 2.5%.

Figure 9C:
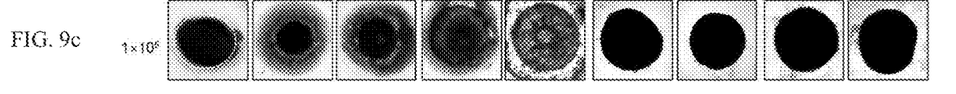
FIG. 9c is the brightfield photographs of organoids over time in examples 4.
Figure 10C:
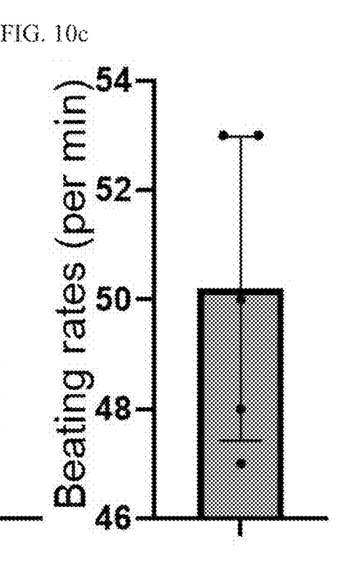
FIG. 10c is the statistical analysis of beating rates of organoids on day 19 in examples 4.

(12) The beating rate/minute of the obtained vascularized cardiac organoids on day 19 reaches approximately 30 beats per minute (as shown in FIGS. 9c, 10c).

It is worth noting that the aforementioned examples are provided solely for the purpose of illustrating the technical scheme of the invention and should not be considered as limiting. While the detailed description of the invention is based on the examples mentioned above, those skilled in the art will understand that the technical scheme outlined in the aforementioned examples may still be subject to modifications and substitutions of some or all of the technical features. Such modifications or substitutions should not depart from the essence of the corresponding technical scheme, as defined within the scope of each example of the invention.

What is claimed is:

1. A preparation method of a vascularized cardiac organoid with a chamber structure, including the following steps:
   step 1: selecting stem cells A and B for in vitro culture and maintenance; wherein the stem cells A are stem cells with vascular lineage cell differentiation potential, and the stem cells B are stem cells with cardiomyocyte differentiation potential;
   step 2: differentiating stem cells A into vascular spheroids and stem cells B into cardiac spheroids;
   wherein step 2 involves culturing the stem cell A into spheroids and subsequently differentiating them into vascular spheroids that express endothelial cell specific marker CD31; alternatively, differentiating the stem cell A into vascular cells under 2D culture conditions and then assembling into spheroids that express endothelial cell specific marker CD31;
   and wherein, step 2 involves culturing stem cell B into spheroids and subsequently differentiating them into cardiac spheroids that express a cardiac specific marker troponin-T (cTNT); alternatively, differentiating the stem cell B into cardiac cells under 2D culture conditions and then assembling into spheroids that express a cardiac specific marker troponin-T (cTNT);
   step 3: fusing one fully differentiated vascular spheroid prepared in step 2 with one cardiac spheroid prepared in step 2 and culturing them to prepare a vascularized cardiac organoid;

wherein, a culture medium used in step 3 CDM3-O supplemented with 20% FBS for the first three days, then from day 4 onwards, the content of FBS is reduced to 2.5%; and wherein the CDM3-O consists of Roswell Park Memorial Institute 1640 (RPMI 1640), 500 μg/mL bovine serum album (BSA) and 200 μg/mL L-ascorbic acid (LAA), 50 ng/mL vascular endothelial growth factor (VEGF), and 25 ng/mL fibroblast growth factor 2 (FGF2);

step 4: obtaining a vascularized cardiac organoid, wherein the vascularized cardiac organoid has an internal chamber structure in the center with an outer layer consisting of myocardium interspersed with a network of blood vessels.

2. The preparation method according to claim 1, wherein the stem cells A and B are selected from animal sourced induced pluripotent stem cells, embryonic stem cells, or adult stem cells.

3. The preparation method according to claim 2, wherein a density of the stem cells A and B maintained in stem cell medium is 80% before passage.

4. The preparation method according to claim 1, wherein the stem cells A and B are selected from human sourced induced pluripotent stem cells, embryonic stem cells, or adult stem cells.

5. The preparation method according to claim 1, wherein the stem cells A and B are derived from pluripotent stem cells, the stem cells are initially cultured into embryoid bodies (EBs) and then divided into two parts, each part is then induced to differentiate into vascular spheroids and cardiac spheroids, respectively.

* * * * *